United States Patent

Falb et al.

[11] Patent Number: 5,197,462
[45] Date of Patent: Mar. 30, 1993

[54] ANESTHETIC METERING DEVICE

[75] Inventors: Wolfgang Falb, Krummesse; Karl-Ludwig Gippert; Ulrich Heim, both of Lübeck; Uvo Hölscher, Stockelsdorf; Siegfried Kiske, Gross Grönau; Götz Kullik, Lübeck; Ralf-Ernst Löser, Kreuzkamp; Christoph Maurer, Bad Schwartau, all of Fed. Rep. of Germany

[73] Assignee: Dragerwerk Aktiengesellschaft, Lubeck, Fed. Rep. of Germany

[21] Appl. No.: 833,328

[22] Filed: Feb. 10, 1992

[30] Foreign Application Priority Data

Feb. 20, 1991 [DE] Fed. Rep. of Germany ....... 4105148

[51] Int. Cl.⁵ .......................................... A61M 16/01
[52] U.S. Cl. ........................... 128/203.14; 128/203.27; 137/101.11
[58] Field of Search .................. 128/203.12, 203.13, 128/203.14, 203.25, 203.26, 203.27; 137/101.11

[56] References Cited

U.S. PATENT DOCUMENTS

| 3,527,213 | 9/1970 | Schreiber | 128/203.25 |
| 3,590,846 | 7/1971 | Eisele | 137/101.11 |
| 3,998,239 | 12/1976 | Kruishoop | 137/101.11 |
| 4,237,925 | 12/1980 | Urushida | 137/552 |
| 4,328,823 | 5/1982 | Schreiber | 137/88 |

FOREIGN PATENT DOCUMENTS

| 709638 | 5/1965 | Canada | 128/203.25 |
| 3342888 | 8/1984 | Fed. Rep. of Germany | 128/203.25 |
| 57929 | 1/1967 | German Democratic Rep. | 128/203.25 |
| 76536 | 3/1950 | Norway | 128/203.25 |
| 1104585 | 2/1968 | United Kingdom | 128/203.14 |
| 1237014 | 6/1971 | United Kingdom | 128/203.25 |

Primary Examiner—Edgar S. Burr
Assistant Examiner—Eric P. Raciti
Attorney, Agent, or Firm—McGlew and Tuttle

[57] ABSTRACT

An anesthetic metering device with a bypass stream 5 passed from a gas inlet opening 2 via a bypass valve 3 to a gas discharge opening 4 and with a vaporizer chamber stream 7 flowing from a vaporizer chamber 6 via an adjusting device. Accurate metering is possible even in the case of anesthetics with low boiling points by manufacturing the vaporizer chamber 6 at least at the saturation vapor pressure of the anesthetic 22. The adjusting device includes a differential pressure transducer 9 connected on both sides of the bypass valve 3 and a metering valve 10, wherein the metering valve 10 is actuated by the output quantity 11 of the differential pressure transducer 9 via a proportional member 12 so that the concentration is adjusted via the variable transmission ratio of the proportional member 12.

4 Claims, 2 Drawing Sheets

ANESTHETIC METERING DEVICE

FIELD OF THE INVENTION

The present invention pertains to an anesthetic metering device with a bypass stream directed from a gas inlet opening via a bypass valve to a gas discharge opening and with a vaporizer chamber stream, which is flowing from a temperature-stabilized vaporizer chamber filled with anesthetic via an adjusting device and enters the bypass stream behind the bypass valve in the direction of flow.

BACKGROUND OF THE INVENTION

An anesthetic metering device of the above-described type in the form of an anesthetic vaporizer has become known from West German Patent No. DE-PS 12,71,903.

In the prior-art anesthetic vaporizer, the gas stream is split at a gas inlet opening into a bypass stream, which directly reaches the gas discharge opening via a bypass valve, and a vaporizer chamber stream, which is led through a vaporizer chamber, is enriched with anesthetic in the vaporizer chamber, and is again fed into the bypass stream behind the bypass valve via an adjusting device. The bypass valve is designed as a pipe throttle and generates in the bypass stream a flow resistance that is a measure for the split ratio of the gas streams through by bypass valve and the vaporizer chamber.

The adjusting device is designed as a cone valve performing stroke movements, with which the anesthetic concentration at the gas discharge opening is adjusted. Under laminar flow conditions, the anesthetic concentration value preselected at the adjusting device depends only slightly on the value of the total stream, since the flow resistance at the bypass valve changes in proportion to the gas stream, and the ratio of the bypass stream to the vaporizer stream consequently changes in the same manner. To compensate for temperature effects, a temperature stabilizer, which is designed as a water reservoir and stabilizes the anesthetic to the temperature T, is provided in the vaporizer chamber. Within the vaporizer chamber, the vaporizer chamber stream is enriched with anesthetic up to the saturation concentration value determined by the temperature T. Thus, on uniting the vaporizer chamber stream with the bypass stream, a maximum anesthetic vapor volume that can be metered is set by the saturation concentration value.

One disadvantage of the prior-art anesthetic vaporizer is the fact that it can be used only to meter an anesthetic whose boiling point is markedly above the operating temperature. If this condition is not met, anesthetic vapor will enter the bypass stream due to boiling anesthetic, as a result of which undefined concentration ratios will appear, which make accurate metering impossible.

In a metering device for anesthetic gases known from Austrian Patent No. AU-PS 58,523/73, the gas stream—here, oxygen—is passed through a vacuum-generating venturi tube acting as a bypass valve, and the anesthetic gas is fed into the stream by means of a diaphragm-controlled valve acting as an adjusting device, as a function of the vacuum becoming established over the venturi tube. The vacuum relative to the atmospheric pressure serves as the regulated quantity for metering on the diaphragm-controlled valve.

It is disadvantageous in the metering device that no provisions are made for accurately setting the concentration, and the adjustment of the amount of anesthetic gas metered is possible only as a function of a vacuum relative to the atmospheric pressure, rather than in proportion to the oxygen gas stream. In addition, pressure variations at the gas discharge opening, as a consequence of, e.g., the respiration pressure, directly affect the vacuum at the venturi tube and consequently the metering of the anesthetic gas as well.

SUMMARY AND OBJECTS OF THE INVENTION

Therefore, the basic object of the present invention is to improve an anesthetic metering device so that accurate metering of the anesthetic concentration is possible even in the case of anesthetics with low boiling points and anesthetic in vapor form is added in proportion to the gas stream.

To accomplish the task, the vaporizer chamber is maintained at least at the saturation vapor pressure of the anesthetic that corresponds to the temperature T, and the adjusting device consists of a differential pressure transducer connected to both sides of the bypass valve and a metering valve in the vaporizer chamber stream, wherein the metering valve is actuated by the output quantity of the differential pressure transducer via a proportional member so that the concentration is set via a variable transmission ratio of the proportional member.

The essential advantage of the present invention is the fact that the temperature-stabilized vaporizer chamber is maintained at least at the saturation vapor pressure of the anesthetic at the temperature T, as a result of which the anesthetic is prevented from boiling. The saturation vapor pressure can be set by selecting the temperature T in the vaporizer chamber. The differential pressure transducer connected in parallel to the bypass valve generates an output quantity that is proportional to the pressure drop over the bypass valve and consequently the bypass stream. With a proportional member, which is driven by the output quantity of the differential pressure transducer, the metering valve in the vaporizer chamber stream is brought into the open position. By varying the transmission ratio of the proportional member, it is possible to set the concentration, because the change in the transmission ratio leads—at equal output quantity on the differential pressure transducer—to different regulating distances or opening positions at the metering valve, and consequently also to different volumes, per unit time, of the anesthetic vapor being released into the bypass stream.

It is advantageous to design the proportional member as a rocker arm mounted in a fulcrum, whose free ends are connected to the differential pressure transducer, on the one hand, and to the metering valve, on the other hand, in such a way that a change in distance, e.g., the deflection of a diaphragm, which corresponds to the differential pressure, is transmitted by the preselected transmission ratio at the rocker arm to the metering valve and the latter is brought into the open position. The transmission ratio can be adjusted by displacing the fulcrum on the rocker arm. However, exclusively electrical solutions are also possible, besides the mechanical transmission of a change in distance. Thus, the output quantity of the differential pressure transducer may be an electrical voltage, and the proportional member may be a variable-gain amplifier. The output voltage of the amplifier is then transformed with an electric motor type (or solenoid) final control element into a corresponding open position of the metering valve.

In another advantageous embodiment, the vaporizer chamber is maintained at least at the saturation vapor pressure, and the adjusting device consists of a differential pressure transducer connected to both sides of the bypass valve and a metering valve actuated by its output quantity in the vaporizer chamber stream, and to set the concentration, the bypass valve is provided with a final control element that changes the flow resistance. Thus, the bypass valve may be designed, for example, as a bevel seat valve that is brought more or less into the open position, depending on the concentration to be set, as a result of which the output quantity at the differential pressure transducer will change in the same manner and lead to a corresponding adjustment on the metering valve.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
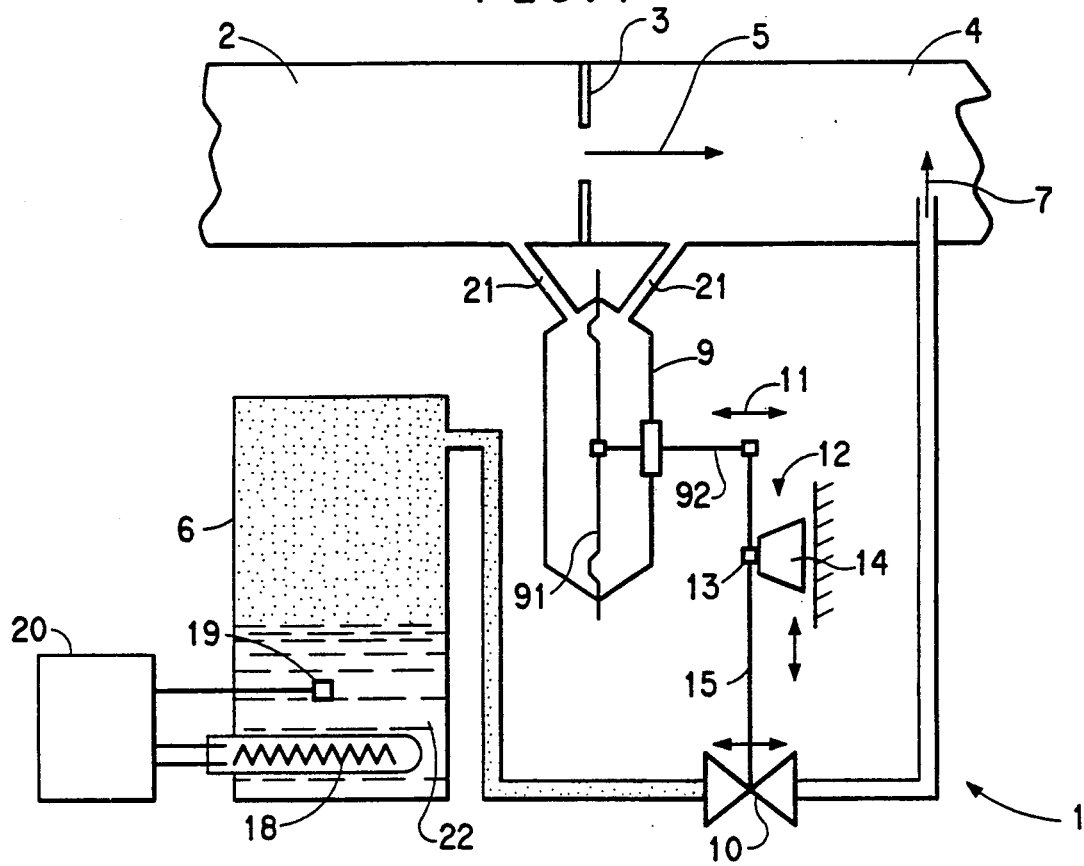
FIG. 1 is a schematic view of an anesthetic metering device with a proportional member for setting the concentration.

In the anesthetic metering device 1 shown in FIG. 1, a bypass stream 5 flows from a gas inlet opening 2 via a bypass valve 3 to a gas discharge opening 4. From a vaporizer chamber 6, which is filled with anesthetic 22 and is maintained at a constant temperature T by means of a heating coil 18, a temperature sensor 19 and a control device 20, a vaporizer chamber stream 7 is mixed with the bypass stream 5 via a metering valve 10. A differential pressure transducer 9, which is designed as a siphon diaphragm, with a diaphragm 91 and a control bar 92 transmitting the deflection of the diaphragm, is connected in parallel to said bypass valve 3 via pressure lines 21. Said control bar 92 transmits the diaphragm deflection, which is the output quantity 11 of said differential pressure transducer 9, to a rocker arm 15, which is mounted with a fulcrum support 14 in a fulcrum 13.

The other end of said rocker arm is connected to a metering valve 10, as a result of which the latter can be brought more or less into the open position depending on the output quantity 11. Said fulcrum 13 is displaceable on said rocker arm, as a result of which the transmission ratio between said output quantity 11 and the regulating distance of said metering valve is adjustable. Said rocker arm 15 and said fulcrum support 14 with said fulcrum 13 form the proportional member 12. The adjusting device for metering said vaporizer chamber stream 7 is composed of said differential pressure transducer 9, said proportional member 12, and said metering valve 10.

During operation, said anesthetic 22 in said vaporizer chamber 6 is first brought with said heating coil 18 to the temperature T above the ambient temperature, after which the corresponding saturation vapor pressure with the corresponding saturation concentration within said vaporizer chamber 6 is adjusted. The temperature T of said anesthetic 22 is measured with said temperature sensor 19 and is sent to a control device 20. It is compared with a stored temperature set value there, and the current flowing through said heating coil 18 is subsequently adjusted correspondingly with said control device 20. Said bypass stream 5 generates at said bypass valve 3 a pressure drop, which deflects said diaphragm 91 of said differential pressure transducer 9 and deflects said rocker arm 15 via said control bar 92. Depending on the position of said fulcrum support 14, the end of said rocker arm 15 connected to said metering valve 10 is deflected correspondingly, and said metering valve 10 is brought into the open position. Depending on the value of the dynamic pressure at said bypass valve 3, said vaporizer chamber stream 7 is metered into said bypass stream 5. By adjusting said fulcrum support 14, i.e., by displacing the fulcrum 13 on said rocker arm 15, the transmission ratio is changed, and it is possible to set, e.g., in the case of constant bypass stream 5, i.e., constant output quantity 11, different regulating distances on said metering valve 10 and consequently different concentrations as said gas discharge opening 4.

Figure 2:
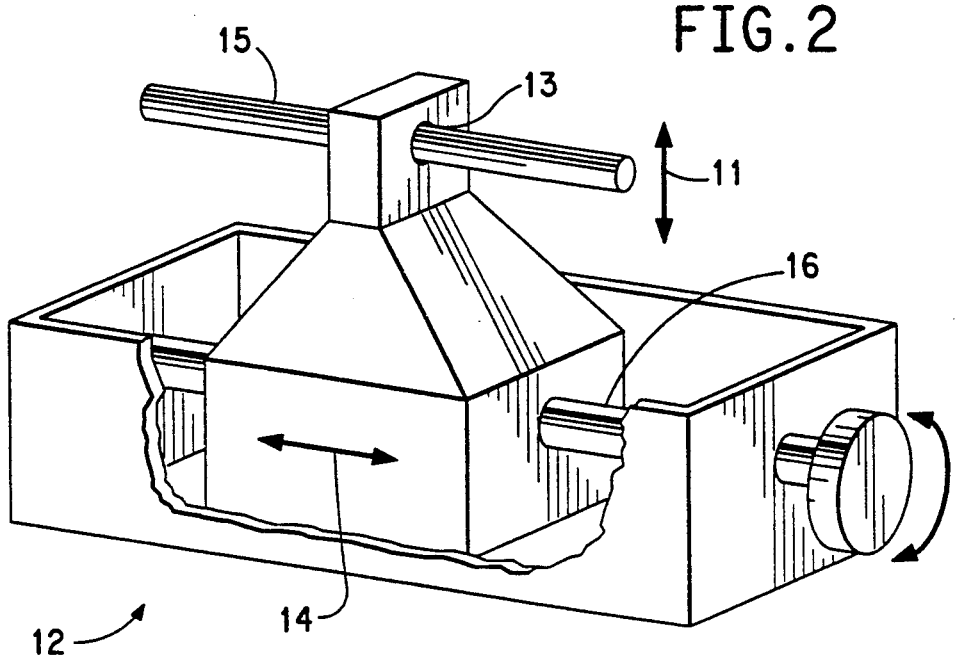
FIG. 2 is the side view of the proportional member.

FIG. 2 shows a side view of said proportional member 12. Identical components are designated with the same reference numerals as in FIG. 1. Said rocker arm 15 is mounted in said fulcrum 13 and is deflected by said output quantity 11 of said differential pressure transducer 9, which is not shown in FIG. 2. Said fulcrum 13 is axially displaceable on said rocker arm 15 by means of said fulcrum support 14, whose location can be changed by a spindle drive 16. As a result, it is possible to set different transmission ratios for said output quantity 11 and consequently different concentration values, corresponding to the leverage laws known from physics.

Figure 3:
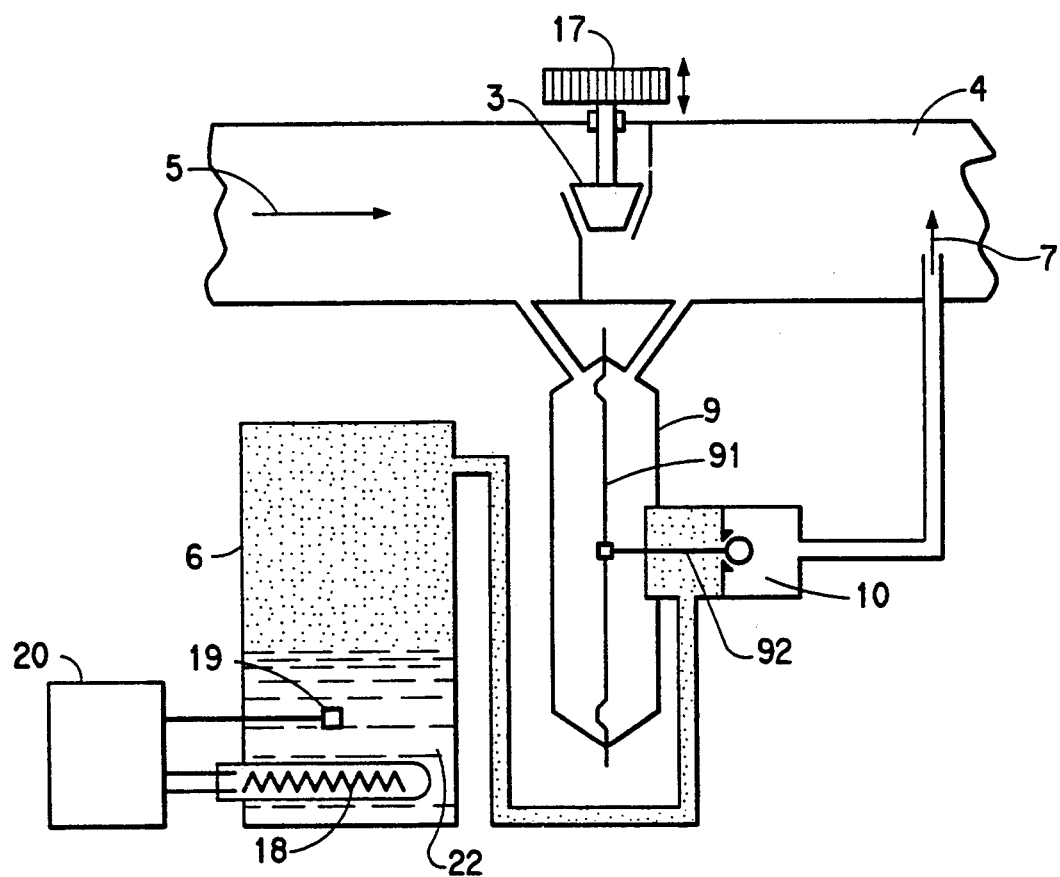
FIG. 3 is an anesthetic metering device with an adjustable bypass valve for setting the concentration.

FIG. 3 shows an alternative embodiment for an anesthetic metering device. Identical components are designated with the same reference numerals as in FIG. 1 and FIG. 2. Said differential pressure transducer 9, connected in parallel to said bypass valve 3, transmits the deflection of said diaphragm 91 with said control bar 92 to said metering valve 10. Depending on the value of the differential pressure at said bypass valve 3, said metering valve 10 is opened more or less completely, and a corresponding vaporizer chamber stream 7 is mixed with said bypass stream 5.

The flow cross section of said bypass valve 3 can by varied by means of a final control element 17. Depending on the position of said final control element 17, a corresponding change will occur at said differential pressure transducer 9, as a result of which said vaporizer chamber stream 7 will be influenced. By making a change at said final control element 17, the anesthetic concentration at said gas discharge opening 4 can be adjusted.

What is claimed is:
1. Anesthetic metering device, comprising:
 a bypass stream flowing from a gas inlet opening via a bypass valve to gas discharge opening;
 a temperature-stabilized vaporizer chamber partially filled with liquid anesthetic, said vaporizer chamber including temperature stabilizing means for maintaining said vaporizer chamber at least at a saturation vapor pressure of the anesthetic corresponding to a temperature T to provide vapor anesthetic in said temperature stabilizer vaporizer chamber, above said liquid anesthetic;

a vaporizer chamber stream means for flow of vapor anesthetic from said temperature-stabilized vapor chamber to said bypass stream, down stream of said bypass valve; and adjusting means including a differential pressure transducer connected on both sides of said bypass valve for generating an output and metering means in said vaporizer chamber stream, said metering means being actuated by said output of said differential pressure transducer via a proportional member having a variable setting, for metering of vapor anesthetic into said bypass stream for adjusting concentration of vapor anesthetic in said bypass stream based on said variable setting of said proportional member.

2. Anesthetic metering device according to claim 1, wherein said proportional member is a rocker arm mounted in a fulcrum, a fulcrum support being provided which is axially displaceable to adjust said transmission ratio via a spindle drive.

3. Anesthetic metering device, comprising:
a bypass stream flowing from a gas inlet opening via a bypass valve to a gas discharge opening;

a temperature controlled vaporizer chamber partially filled with liquid anesthetic, said vaporizer chamber including temperature stabilizing means for maintaining said vaporizer chamber at least at a saturation vapor pressure of the anesthetic corresponding to a temperature T to provide vapor anesthetic in said temperature stabilized vaporizer chamber, above said liquid anesthetic;

a vaporizer chamber stream means for flow of vapor anesthetic from said temperature-control vaporizer chamber to said bypass stream, downstream of said bypass valve; and adjusting means including a differential pressure transducer connected to each side of said bypass valve for generating an output and a metering valve in said vaporizer chamber stream, said metering valve being actuated by said output of said differential pressure transducer, said bypass valve including control means for changing flow resistance to adjust concentration of vaporized anesthetic in said bypass stream.

4. An anesthetic metering device, comprising:
a bypass stream conduit extending from a gas inlet opening to a gas discharge opening;

a bypass valve positioned in said bypass stream conduit;

a temperature-stabilized vaporizer chamber partially filled with liquid anesthetic, said vaporizer chamber including temperature stabilizing means for maintaining said vaporizer chamber at least at a saturation vapor pressure of the anesthetic corresponding to a temperature T, to provide vapor anesthetic in said temperature stabilized vaporizer chamber, above said liquid anesthetic;

a vaporizer chamber stream conduit, connected to said temperature-stabilized vaporizer chamber and having an end extending into said bypass stream conduit with an opening for the flow of vapor anesthetic into said bypass stream conduit;

metering means connected to said vaporizer chamber stream conduit for metering vapor anesthetic into said bypass stream conduit; and adjusting means for adjusting said metering means to vary a concentration of vapor anesthetic in said bypass stream, said adjusting means including a differential pressure transducer connected on both sides of said bypass valve for generating an output and control means for conditioning said output for adjusting concentration of vapor anesthetic in said bypass stream.

* * * * *